United States Patent
Steger

(10) Patent No.: US 9,937,024 B2
(45) Date of Patent: Apr. 10, 2018

(54) AXIALLY ELONGATE DENTAL MACHINING PORTION

(71) Applicant: Heinrich Steger, Bruneck (IT)

(72) Inventor: Heinrich Steger, Bruneck (IT)

( * ) Notice: Subject to any disclaimer, the term of this patent is extended or adjusted under 35 U.S.C. 154(b) by 889 days.

(21) Appl. No.: 14/333,572

(22) Filed: Jul. 17, 2014

(65) Prior Publication Data

US 2015/0099243 A1    Apr. 9, 2015

(30) Foreign Application Priority Data

Oct. 9, 2013  (AT) ........................ 326/2013
Jan. 17, 2014  (AT) ........................ 18/2014

(51) Int. Cl.
*B23C 5/00*    (2006.01)
*A61C 13/00*   (2006.01)
(Continued)

(52) U.S. Cl.
CPC ............ *A61C 13/0022* (2013.01); *A61C 5/77* (2017.02); *A61C 8/005* (2013.01);
(Continued)

(58) Field of Classification Search
CPC .. A61C 13/0022; A61C 13/08; A61C 13/0004
See application file for complete search history.

(56) References Cited

U.S. PATENT DOCUMENTS 5,342,696 A    8/1994  Eidenbenz et al.
6,224,371 B1 *  5/2001  De Luca .............. A61C 8/0051
                                          264/19
(Continued)

FOREIGN PATENT DOCUMENTS

DE    20 2008 006 553    8/2008
EP         0 480 209     4/1992
(Continued)

OTHER PUBLICATIONS

Machine Translation EP 0904743 A2, which EP '743 was published Mar. 1999.*
Austrian Patent Office Search Report dated Nov. 27, 2013 in Austrian Patent Application No. GM 326/2013 (ASR1).
Austrian Patent Office Search Report dated Feb. 20, 2014 in Austrian Patent Application No. GM 18/2014 (ASR2).

*Primary Examiner* — Erica E Cadugan
(74) *Attorney, Agent, or Firm* — Wenderoth, Lind & Ponack, L.L.P.

(57) ABSTRACT

An axially elongate dental machining portion includes a machining region machinable by a dental machining device, and a fixing region for fixing the axially elongate dental machining portion to a holder of the dental machining device. In the fixing region is a fixing projection oriented transversely relative to a longitudinal axis. In a condition of the machining portion being mounted in the holder, the fixing projection bears against a holding nose positioned in complementary relationship on the holder. The machining region has a machinable surface which has a maximum spacing relative to the longitudinal axis, measured normal to the longitudinal axis, and the fixing projection has a maximum spacing relative to the longitudinal axis, measured normal relative to the longitudinal axis, that is greater than the maximum spacing of the machinable surface relative to the longitudinal axis.

25 Claims, 14 Drawing Sheets

(51) Int. Cl.
  *B23B 31/02* (2006.01)
  *B23B 31/20* (2006.01)
  *A61C 8/00* (2006.01)
  *B23C 3/00* (2006.01)
  *A61C 5/77* (2017.01)
  *B23C 1/04* (2006.01)
  *B24B 19/26* (2006.01)
  *B23Q 3/06* (2006.01)

(52) U.S. Cl.
  CPC ........ *A61C 13/0004* (2013.01); *B23B 31/201* (2013.01); *B23C 3/00* (2013.01); *B23Q 3/062* (2013.01); *B23B 2231/20* (2013.01); *B23B 2231/2005* (2013.01); *B23C 1/04* (2013.01); *B23C 2240/12* (2013.01); *B23C 2270/08* (2013.01); *B23Q 3/061* (2013.01); *B24B 19/26* (2013.01); *Y10T 29/5107* (2015.01); *Y10T 29/5176* (2015.01); *Y10T 279/17504* (2015.01); *Y10T 279/17871* (2015.01); *Y10T 279/17881* (2015.01); *Y10T 409/307168* (2015.01); *Y10T 409/309016* (2015.01)

(56) References Cited

U.S. PATENT DOCUMENTS

| | | | |
|---|---|---|---|
| 6,627,327 | B2 * | 9/2003 | Reidt ............... A61C 13/0022 428/34.1 |
| 8,402,624 | B2 | 3/2013 | Galehr |
| 2006/0035776 | A1 | 2/2006 | Duncan et al. |
| 2009/0075238 | A1 * | 3/2009 | Galehr ............. A61C 13/0022 433/213 |
| 2009/0130634 | A1 | 5/2009 | Ganley et al. |
| 2012/0148985 | A1 * | 6/2012 | Jung .................... A61C 13/08 433/212.1 |
| 2012/0214133 | A1 | 8/2012 | Jung |
| 2012/0233830 | A1 | 9/2012 | Gapp et al. |
| 2012/0237902 | A1 | 9/2012 | Maniscalco |
| 2013/0157222 | A1 | 6/2013 | Yeom |

FOREIGN PATENT DOCUMENTS

| | | |
|---|---|---|
| EP | 0904743 A2 * | 3/1999 |
| EP | 2 036 516 | 3/2009 |
| EP | 2 499 993 | 9/2012 |
| EP | 2 604 219 | 6/2013 |

* cited by examiner

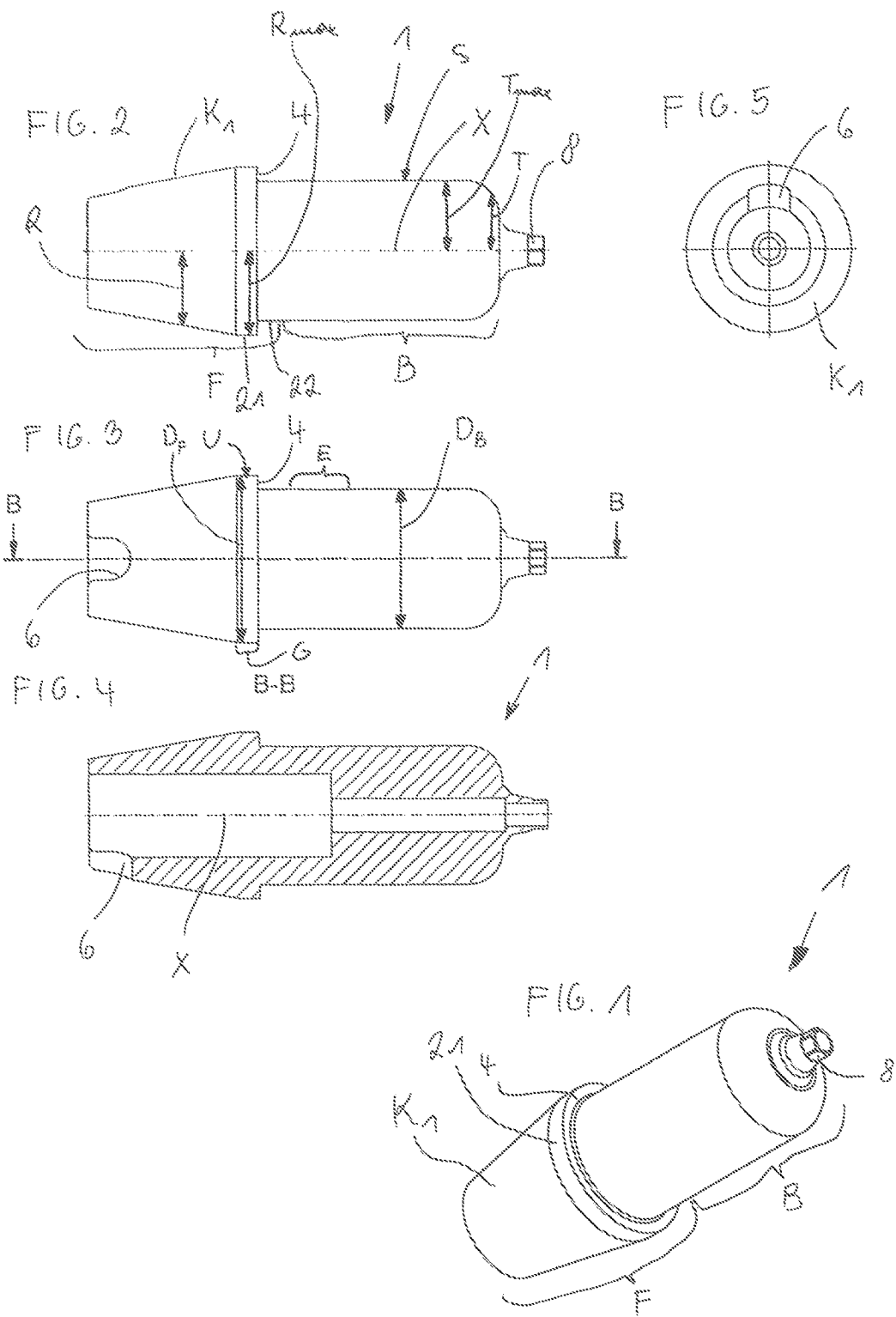

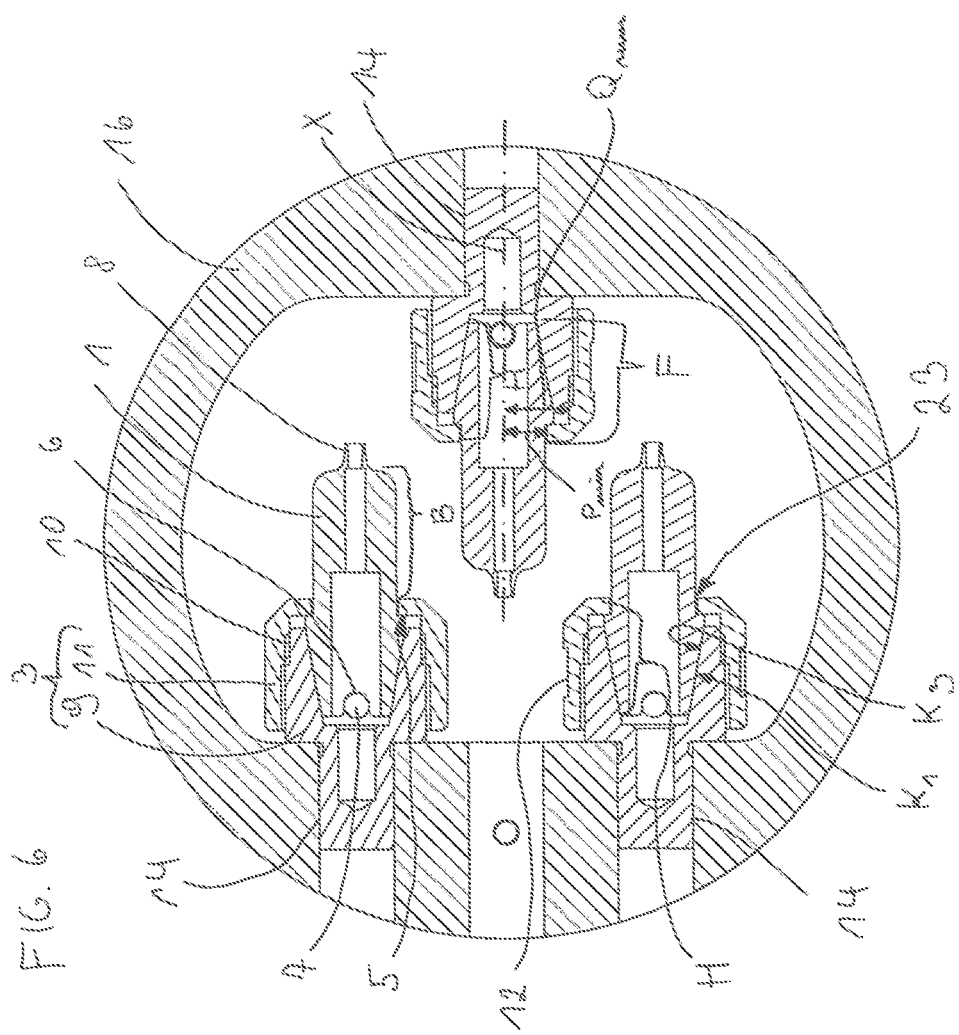

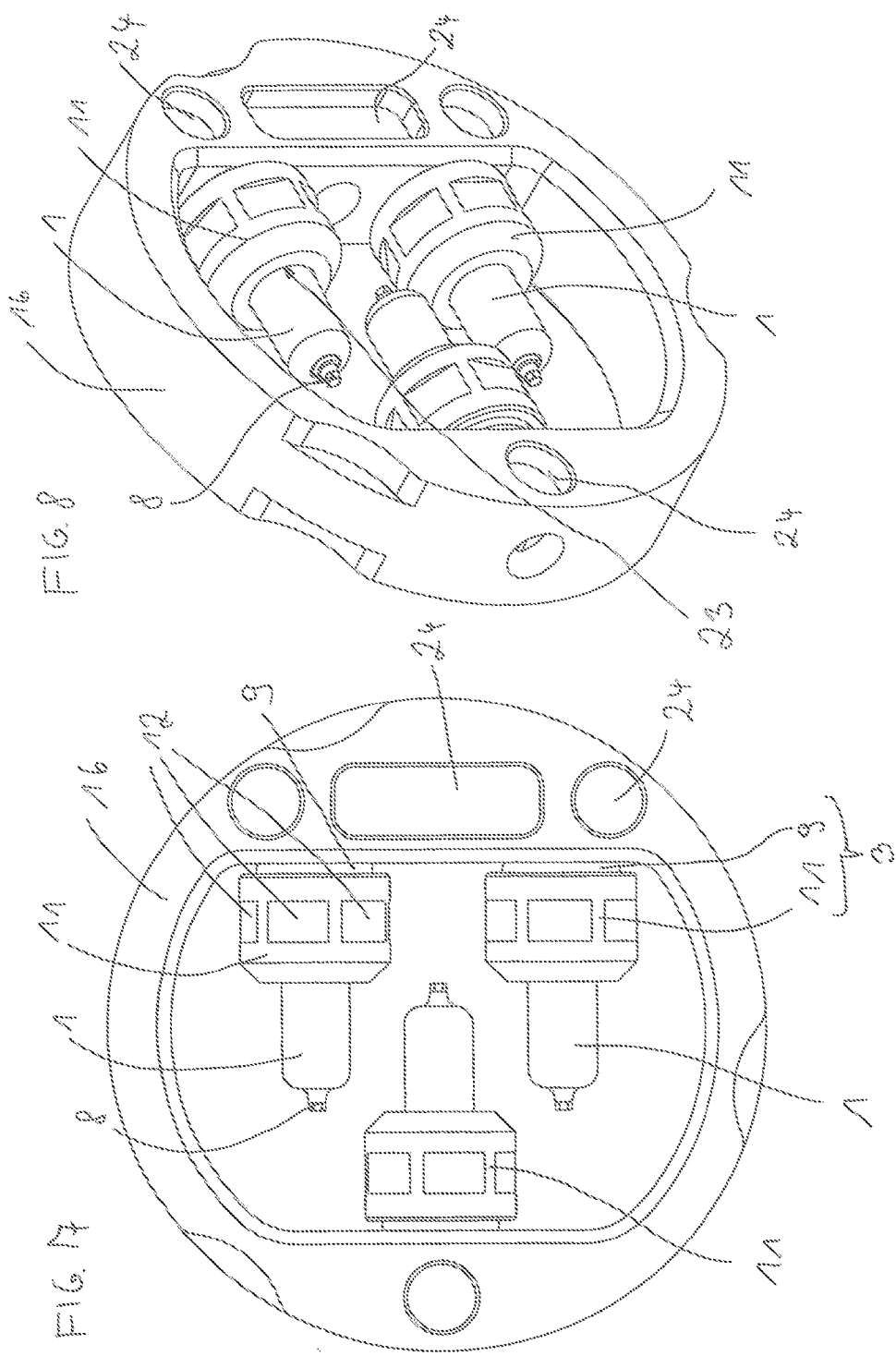

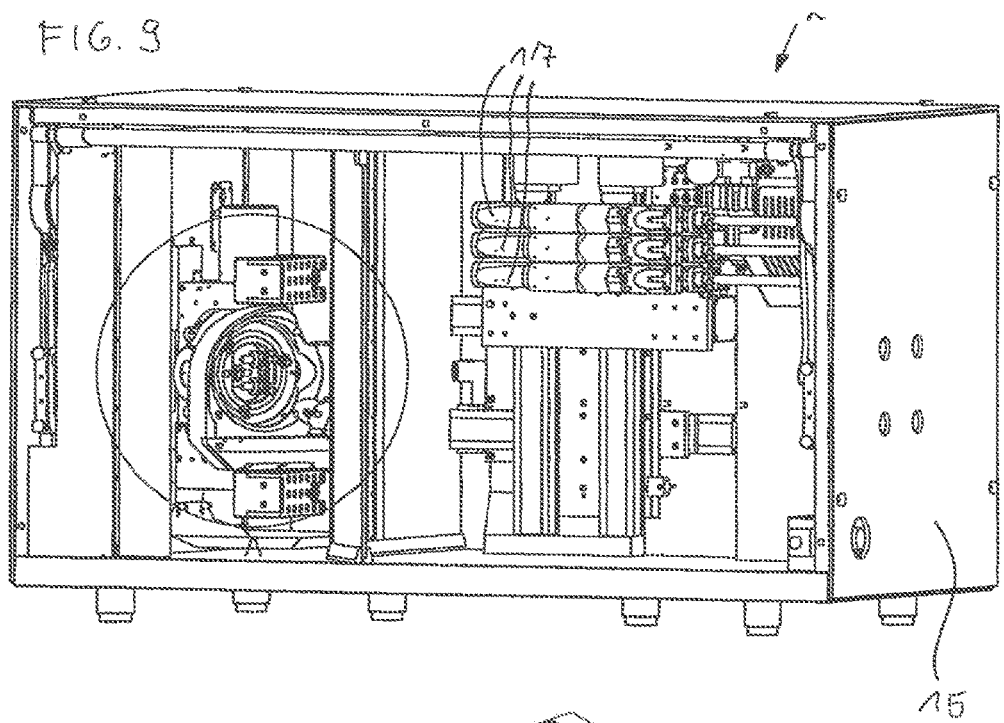
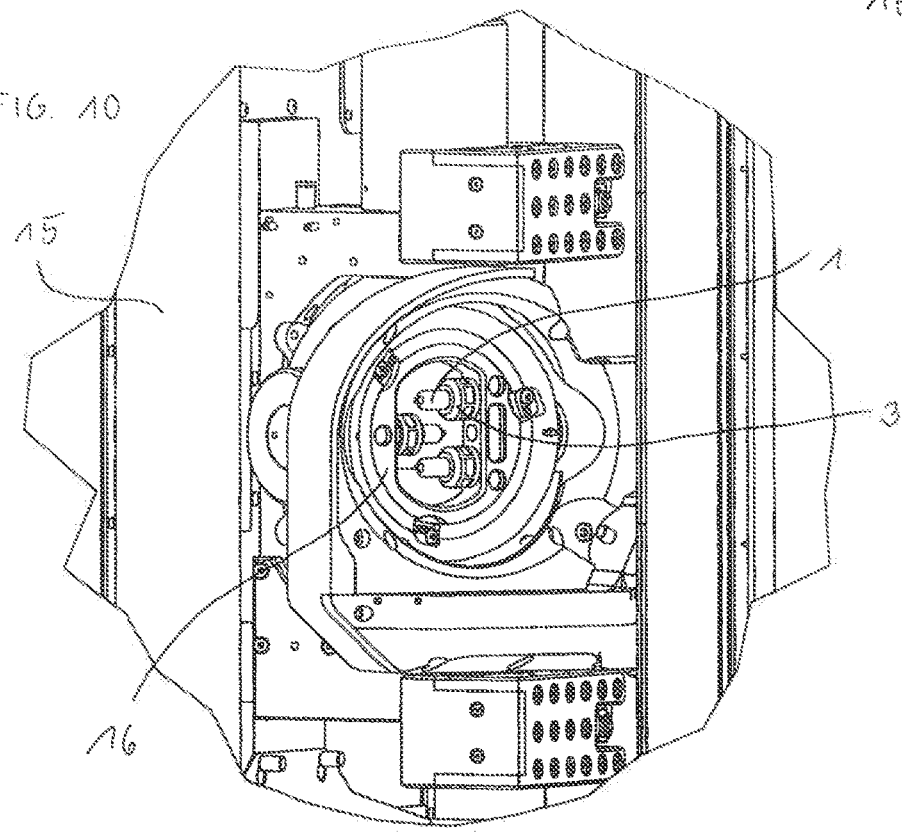

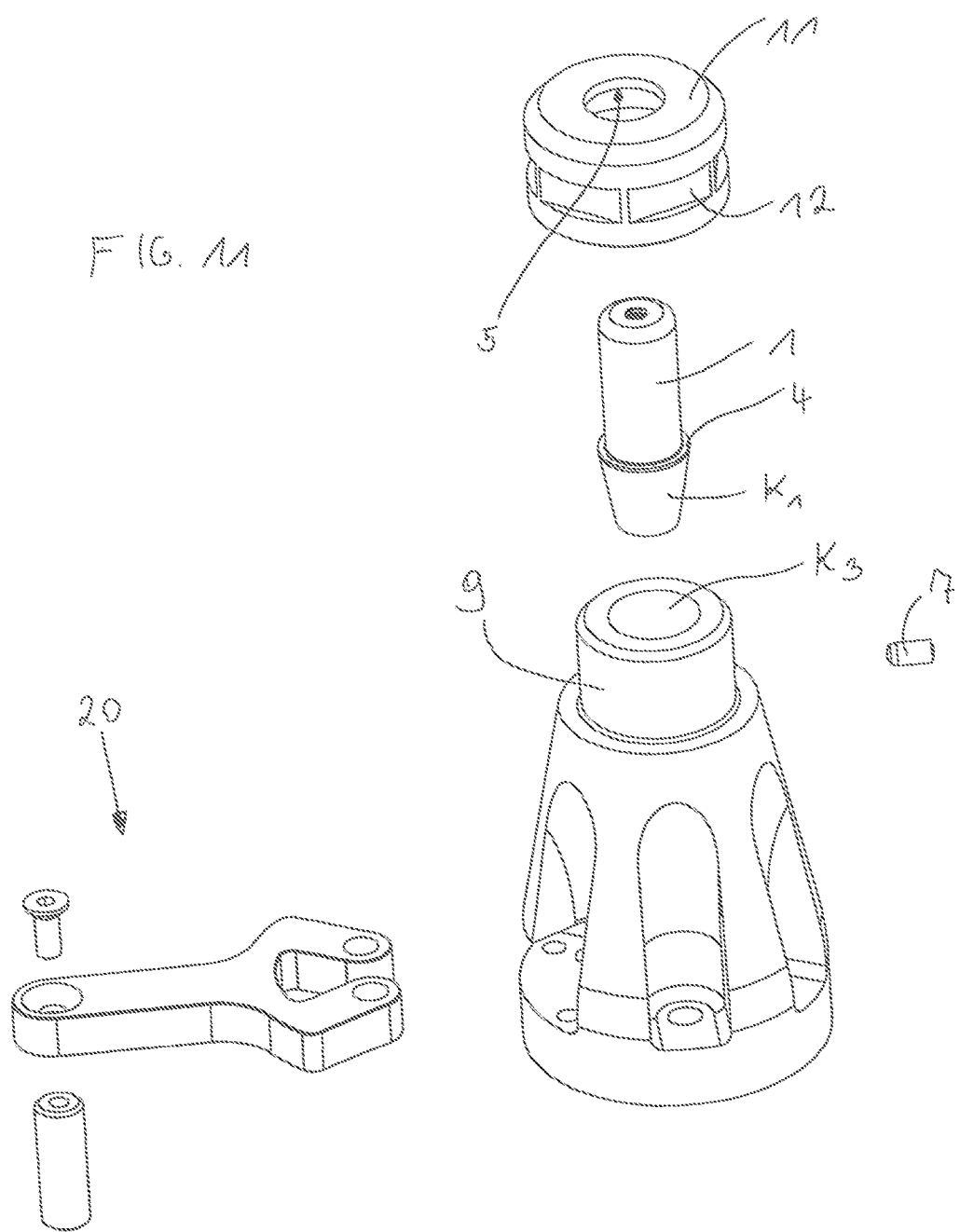

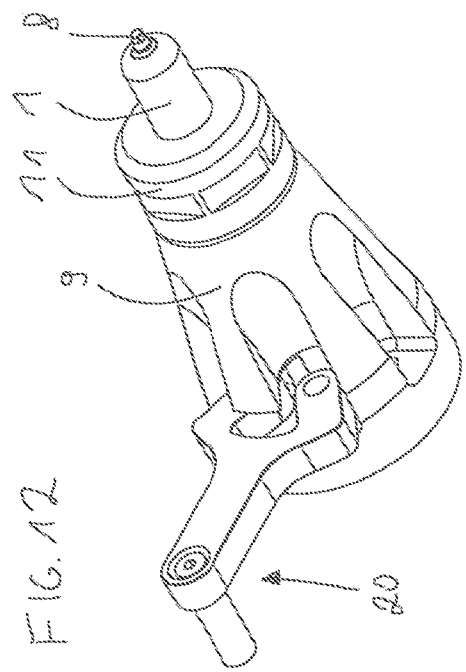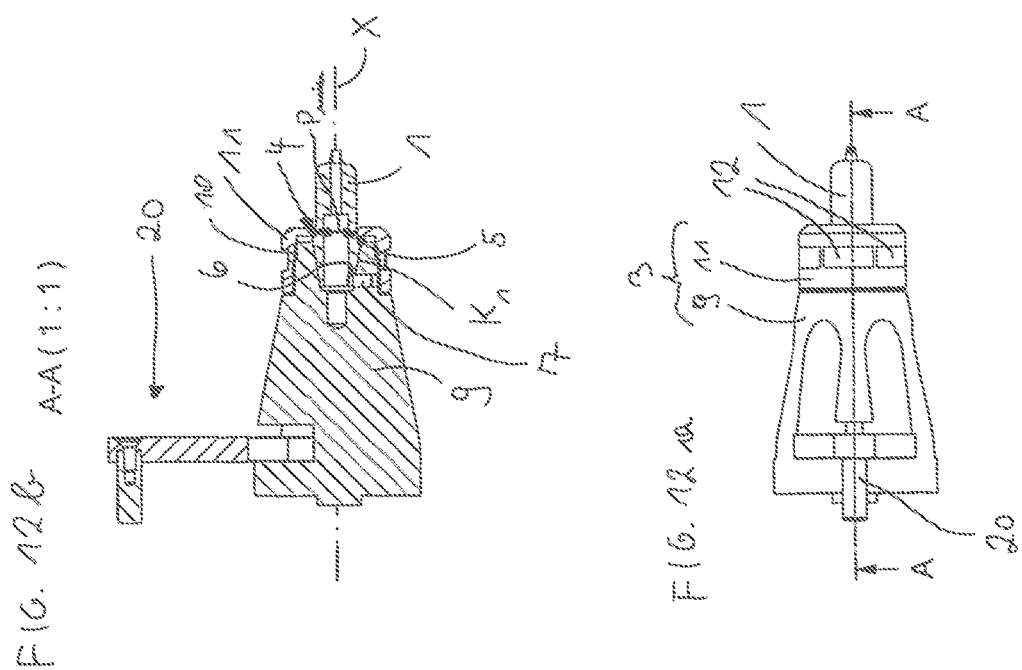

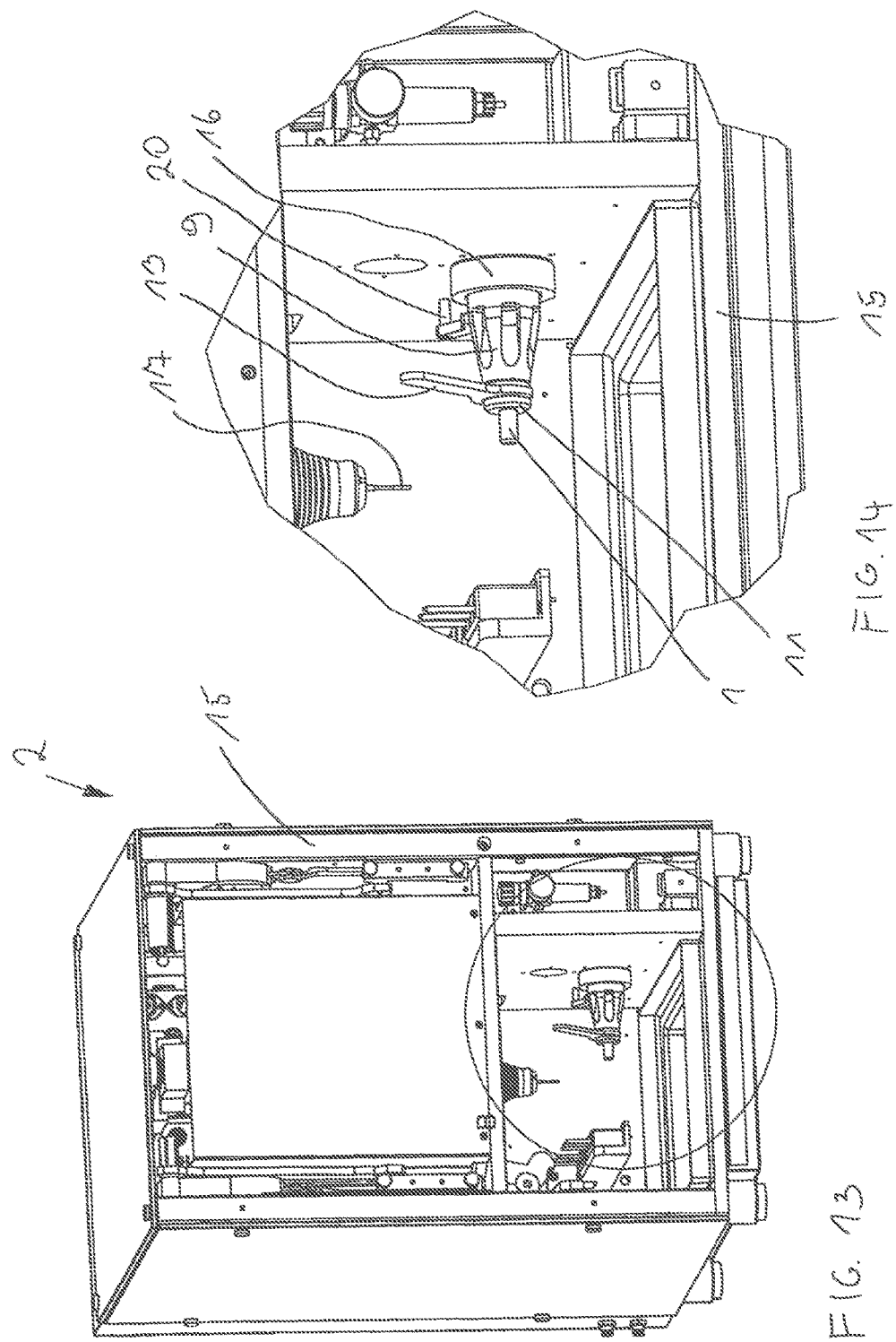

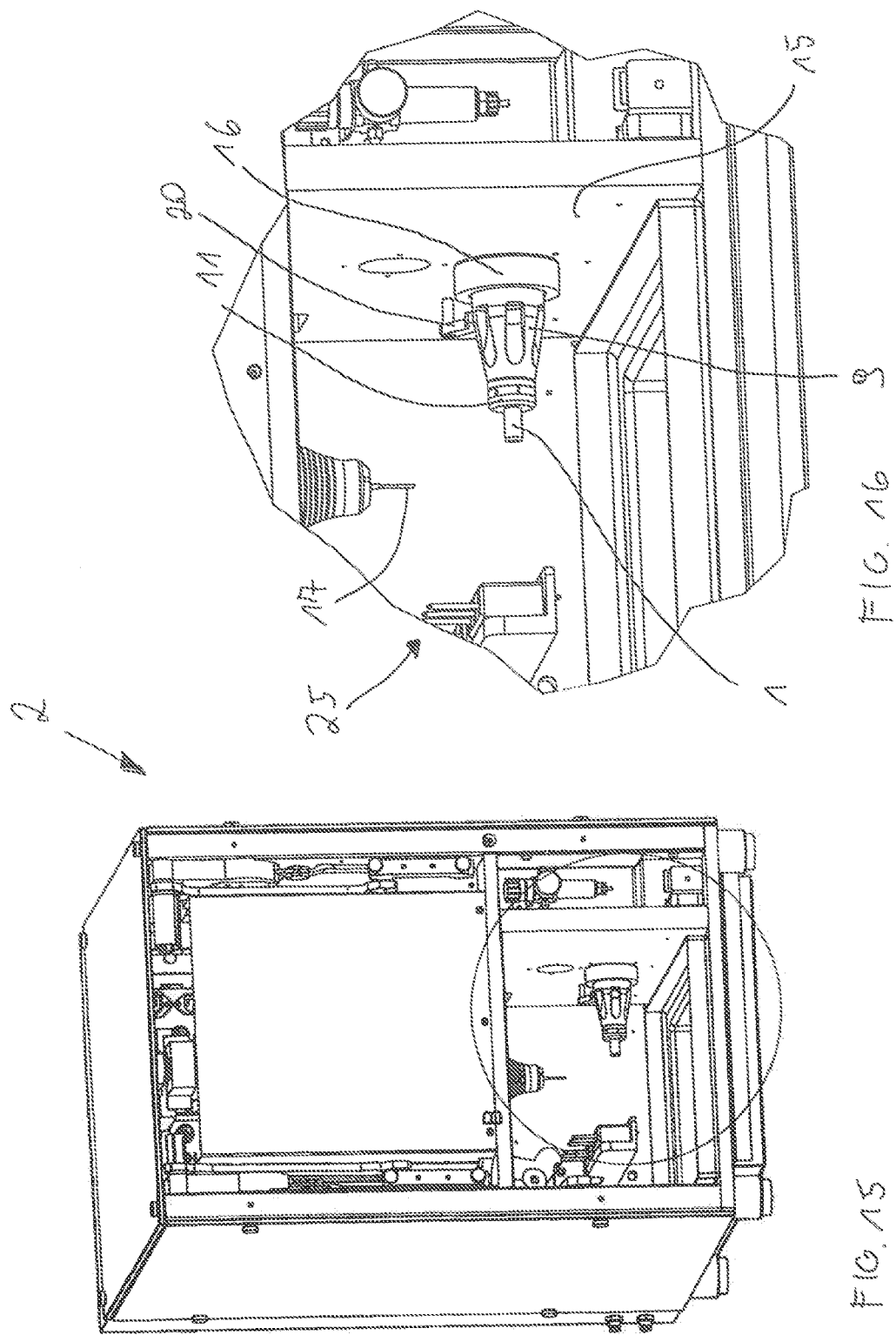

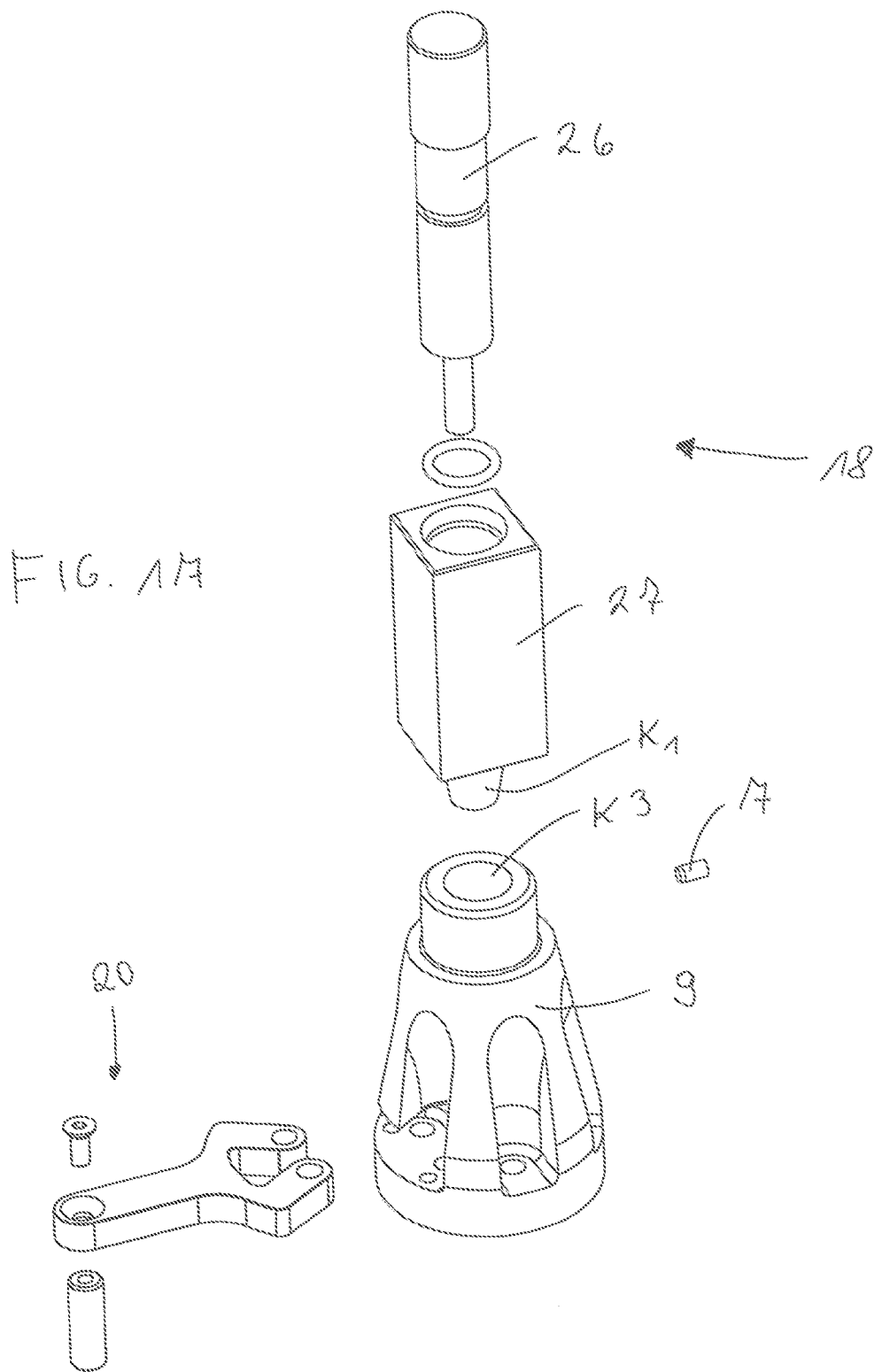

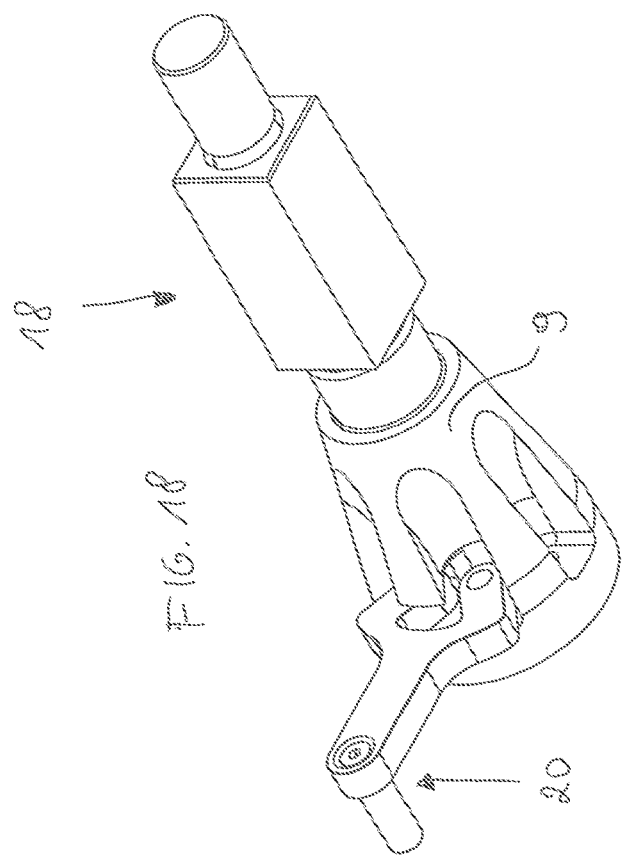
FIG. 18
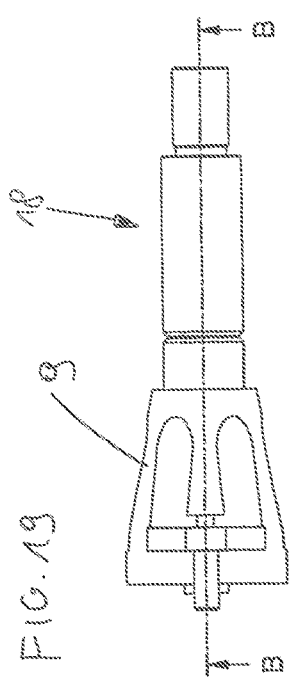
FIG. 19
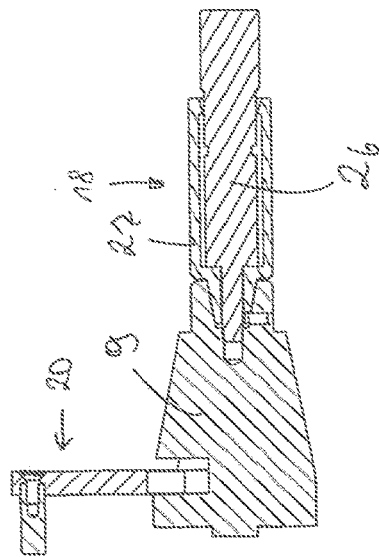
FIG. 20  B-B (1:1)

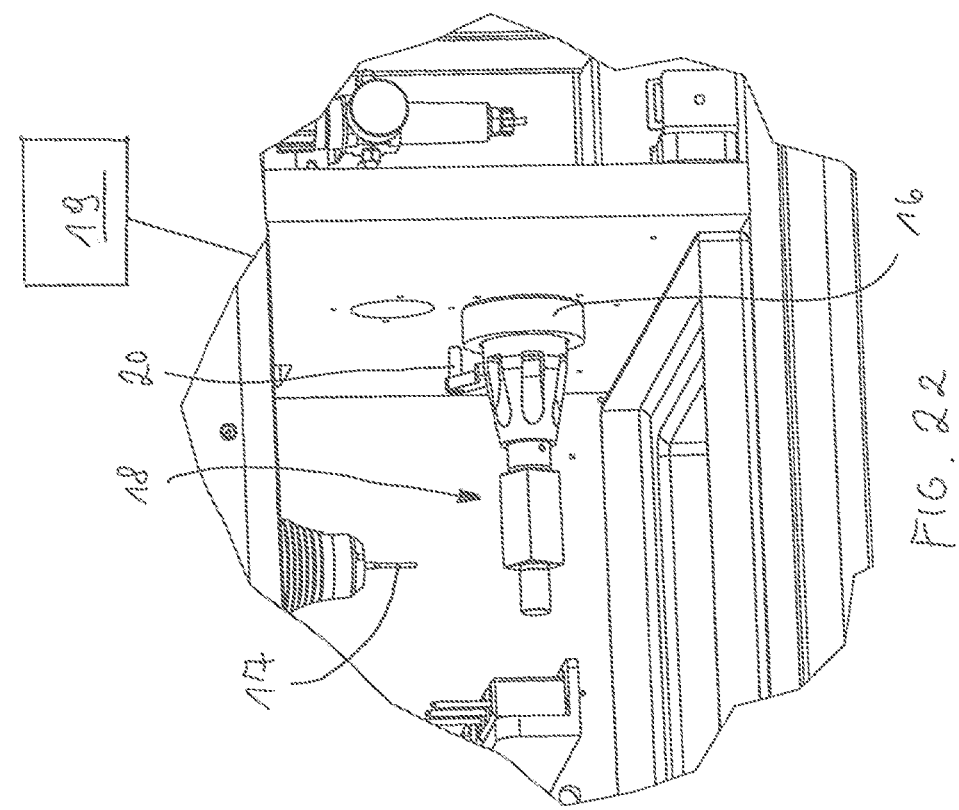
FIG. 2.2
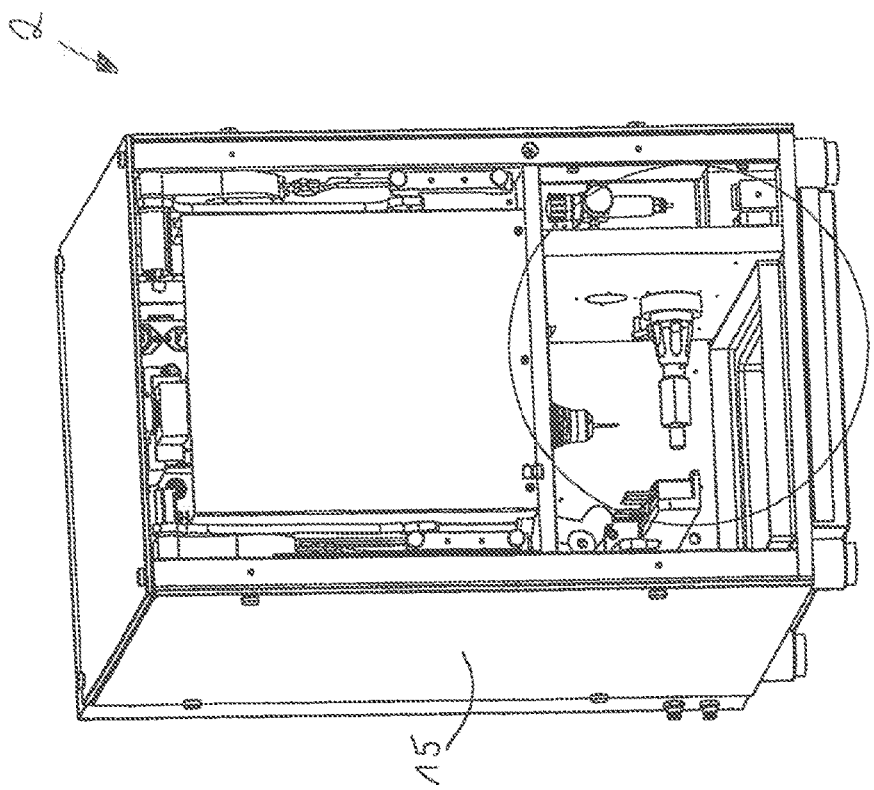
FIG. 2.1

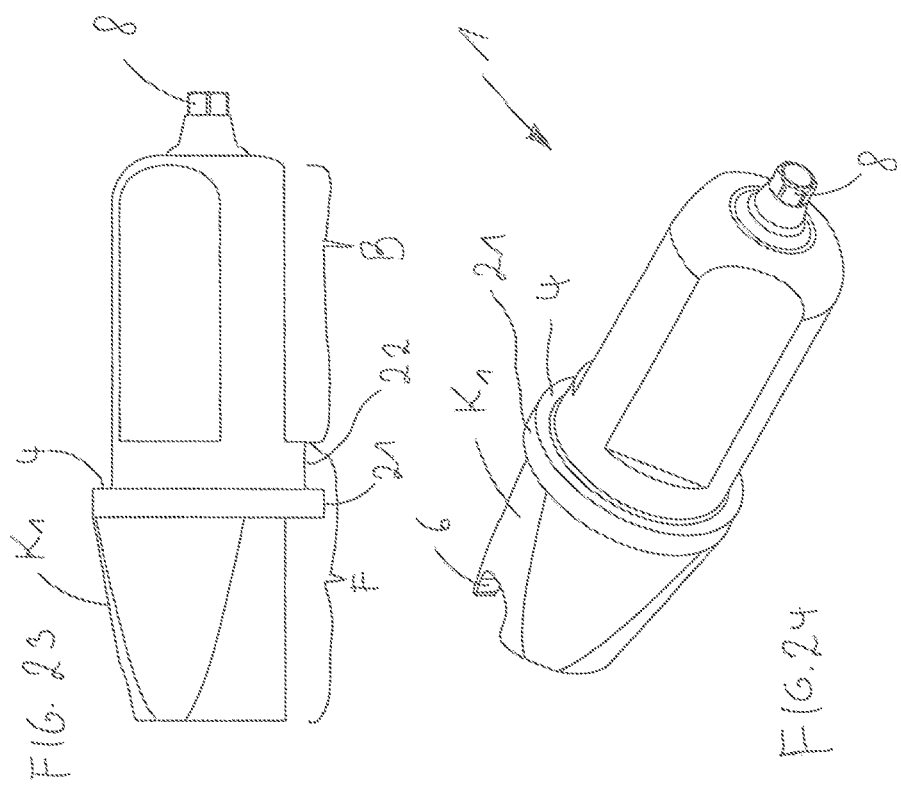

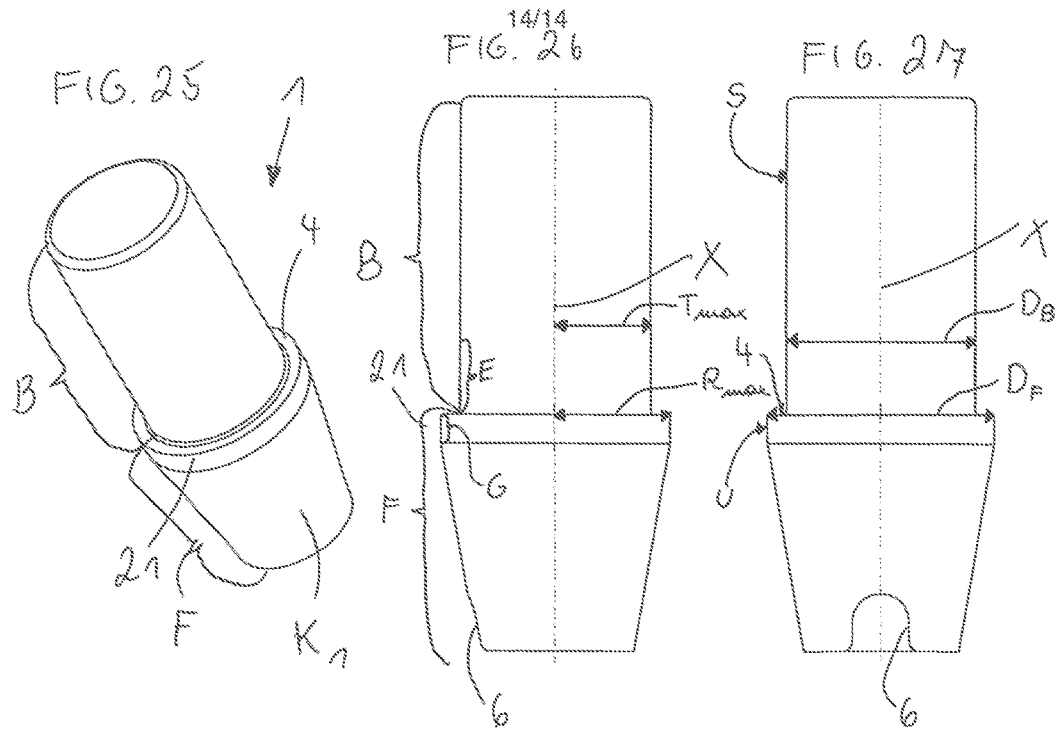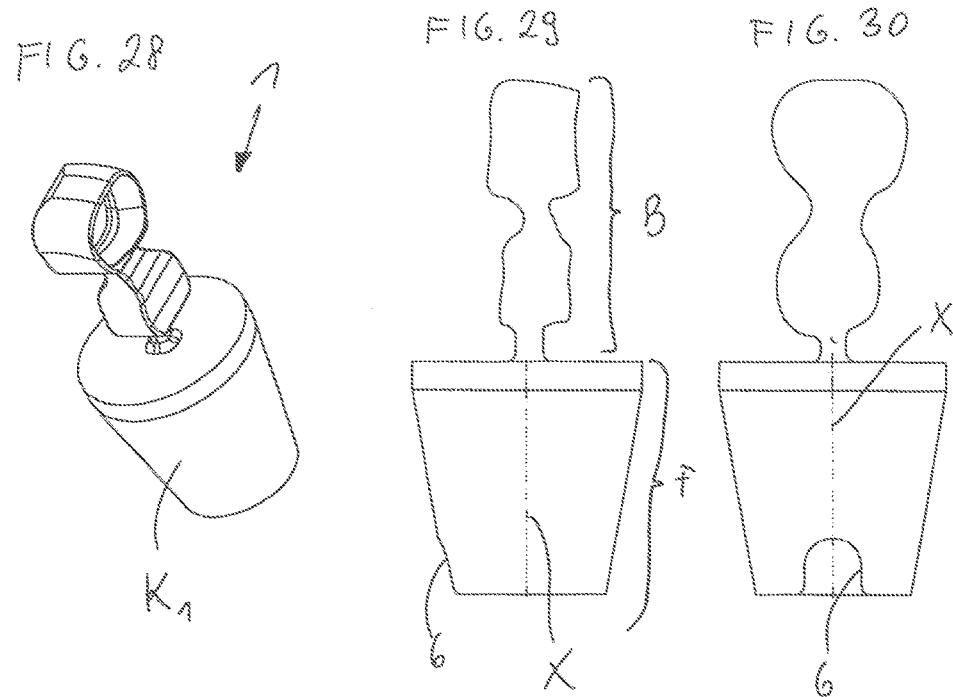

AXIALLY ELONGATE DENTAL MACHINING PORTION

BACKGROUND OF THE INVENTION

1. Field of the Invention

The invention concerns an axially elongate dental machining portion, in particular an abutment or dental construction like a crown or bridge, comprising a machining region machinable by a dental machining device, and a fixing region for fixing the machining portion to a holder of the machining device. The invention also concerns an axially elongate holder for holding a dental machining portion, having a holding region for the dental machining portion. In addition, the invention concerns a set having at least one such machining portion and such a holder. The invention further concerns a dental machining device.

2. Description of the Related Art

There are numerous possible ways in the dental industry of producing various parts which form a dental prosthesis. A variant in that respect is the manual production of various parts. Increasingly, however, in recent times, entire machining devices are also used, with which dental prosthesis parts are produced automatically or semi-automatically. A particular area in that respect is the production of abutments which form a connecting portion between a tooth implant serving as a tooth root prosthesis and the tooth crown which is later visible. Such an abutment forms the delicate and problematical transition between the soft tissue (gum) relative to the oral cavity and the tooth crown. Often such abutments are fitted releasably in the actual tooth implant. Usually abutments are made from titanium, aluminum oxide or zirconium dioxide. A common manufacturing device is a CNC machine which can have various machining heads or grinding, milling or the like. The invention, however, concerns not only such abutments but also machining portions in the form of dental constructions like, for example, crowns and bridges. In that respect, manufacture involves using similar or identical methods and generally identical machining devices.

EP 2 036 516 A2 discloses a blank arrangement in which the blank itself has only a machining region and no direct fixing region for fixing to a machining device. Rather the blank has a fixing surface which is oriented transversely relative to the machining surface and by way of which the blank is glued to a holder. That holder is in turn held in an adapter, wherein provided on the adapter is a notch with which the entire arrangement can be fixed to a tool receiving means of a machining device. The support flange which is wider is thus not part of the blank/abutment or is not in one piece with the blank. Another disadvantage is that the adhesive joint between the blank and the holder can come loose under a heavy loading when machining the blank. In addition, this three-part structure (blank, holder and adapter) is rather complicated and expensive.

DE 20 2008 006 553 U1 is known, wherein a laboratory implant is held to a milling support base. In that case, a clamping chuck and a clamping nut are provided for holding the laboratory implant by way of the manually actuable clamping collet. The entire handling apparatus is held to a work table by way of clamping elements. That work table in turn is associated with a milling machine. A disadvantage with that holding arrangement for a laboratory implant is that an elastic clamping collet is arranged between the laboratory implant and the clamping nut or the clamping chuck, whereby deformation phenomena can occur, which lead to an inaccuracy when machining the laboratory implant. In addition, that design configuration is quite complicated and expensive as at least three different components are required to hold the laboratory implant.

US 2012/0237902 A1 discloses an abutment with a machinable chimney portion which is adjoined by a radially projecting seat region (referred to as a shelf portion). Thereafter, the abutment narrows conically in the shoulder portion. The abutment is fixed or held by way of a base portion. The abutment can be screwed in on a screw portion by way of that base portion which is to be equated to an implant connection. The shelf portion does not serve to fix or hold the abutment and because of its low level of stability it is also not in any way suitable for that purpose but it serves only as a contact surface or abutment portion for a supraconstruction which is to be fitted later. In the machining process, that abutment is screwed onto an implant connection-emulating receiving region by way of the base portion (formed by virtue of the screw thread a kind of fixing projection referred to later). Thus, the machining operation automatically entails a disadvantageous loading on the delicate connection (base portion) due to the vibration occurring in the machining process. In addition, in the machining operation detrimental high lever forces can take effect because of the relatively large spacing between the base portion and the machinable chimney portion EP 2 499 993 A1 discloses a blank in which, however, the blank is not held directly but rather by way of a separately provided shank region. The manufacture of those separate components is relatively complicated and expensive.

The same applies to EP 0 480 209 A1 disclosing a blank body which is glued on a carrier of aluminum which in turn is connected to an anchorage portion on which a latching groove is provided for indirectly holding the blank body to a clamping mounting carrier by way of a holding flange.

In comparison, it is known from EP 2 604 219 A1 for an abutment to be clamped in position directly in a receiving means. That is effected by actuating a screw. The diameter of a recess is reduced by that screw and the abutment is so-to-speak clamped in place in that way. The disadvantage here is that the abutment is only held or clamped in place laterally (in frictionally locking relationship) and there is no (positively locking) fixing in the direction of the longitudinal axis.

Therefore, the invention further concerns a fixing projection provided in the fixing region transversely relative to the longitudinal axis, wherein the fixing projection, in a condition of the machining portion of being mounted in the holder, bears against a holding nose provided in complementary relationship on the holder. That does not involve an indirect connection or holding effect by way of an inaccurate elastic portion, but rather the holder is connected to the machining portion in direct positively locking relationship and which is not based purely on clamping. In other words, the machining portion itself has an external contour with a fixing projection for fixing the machining portion to a holder in positively locking engagement. That also permits good torque transmission if the machining portion is turned in the machining operation.

An inwardly directed groove of that kind, which is comparable to a fixing projection provided in the machining portion, is to be found in US 2009/0130634 A1. A disadvantage there is that the fixing region is relatively narrow in particular due to the groove, whereby the fixing region is fragile and can thus easily fracture when the machining portion is being machined. In addition, experience has shown with such clamping mechanisms that the workpiece can suffer from clamping deformation when a sufficiently high clamping force is involved, and that results in an out-of-roundness. The production of high-precision, prefabricated connections on the abutment would be in vain if the connection is pushed off-center again by the clamping action and the machining device then no longer knows the precise position of the machining portion.

An abutment (blank) having a mandrel is disclosed in US 2006/0035776 A1. The abutment can be fixed by way of a groove in the mandrel in a base corresponding to the mandrel by way of a rotatable cam. That specification shows two different embodiments of the abutment. A disadvantage with the first abutment is a narrowing (referred to as the sprue) between the front portion to be machined and the mandrel, which can easily fracture in the machining operation. In the second embodiment, the region of the groove is quite narrow. This therefore involves a poor hold. In addition, the mandrel can easily fracture in that region under a heavy load. That narrow location forms a connector which is retained to prevent the part from uncontrolledly dropping down. That location is usually produced entirely at the end of the manufacturing process after the geometrically important regions have already been machined. The workpiece is later then manually separated off, which, due to the narrow location, no longer represent a problem. A disadvantage in both embodiments is that the fixing region (groove) is quite far from the front portion to be machined. That relatively great distance means that the forces and stresses in the machining operation can be increased due to the lever action, whereby damage can easily happen.

US 2012/0214133 A1 also discloses a kind of fixing projection which, however, is formed internally in the abutment. Using a screw which can be passed through the abutment and which can be screwed to a connector, the abutment is held and clamped in positively locking relationship between the connector and the head of the screw. A disadvantage here is also that the shank of the abutment is very narrow and is thus rather fragile. The blank is clamped at its most delicate part, namely the connection to the implant, where a weakening and deformation of that connection occurs in a machining operation. The relatively thin screw is also already no longer able to withstand somewhat higher loading levels. A further disadvantage is that it is only possible to produce hollow machining portions as fixing in fact is effected by way of the hollow bore. This means that a complicated and expensive operation of filling that hollow bore always has to be performed subsequently in a separate step.

SUMMARY OF THE INVENTION

Therefore, the object of the present invention is to provide a machining portion which is improved over the state of the art, and an improved holder. In particular, the invention seeks to provide that fixing or holding of the machining portion to a holder is simplified. The invention further seeks to provide that fixing can be effected as precisely and stably as possible.

Accordingly, it is provided in accordance with the invention that the machining region has a machinable surface which has a maximum spacing relative to the longitudinal axis, measured normal to the longitudinal axis, and the fixing projection has a maximum spacing relative to the longitudinal axis, measured normal relative to the longitudinal axis, that is greater than the maximum spacing of the machinable surface relative to the longitudinal axis. In other words, the fixing projection is the widest region of the entire machining portion and forms an abutment for a holder, that is directed outwardly or that leads away from the longitudinal axis. In that way, the machining portion can be fixed directly by way of the relatively wide and thus very stable fixing projection. In addition, there is no need for a hollow bore in the machining portion.

The fixing projection preferably has a flat surface. To achieve a mechanical hold which is as good as possible, that surface or the fixing projection should be oriented at an angle of between 10 and 170 degrees relative to the longitudinal axis. The angle range is preferably between 45 and 135 degrees. Particularly preferably, that range is between 70 and 110 degrees. Ideally, the fixing projection is oriented at an angle of 90 degrees relative to the longitudinal axis.

In principle, the fixing projection can be provided only in a relatively small region on the machining portion. It is preferably provided, however, that the fixing projection is of an annular configuration on the machining portion. Thus, the fixing projection surrounds the entire machining portion. In other words, the fixing projection is provided around the entire machining portion and is wider throughout than the machining region.

For simple and nonetheless precise introduction of the machining portion into the holder, it is preferably provided that there is a conical region in the fixing region, wherein the conical region, in a condition of the machining portion of being mounted in the holder, bears against a conical region of a complementary configuration on the holder. In that way, it is also possible to apply a relatively high clamping force, achieve good concentricity and attain good rotational truth.

In principle, the dental machining portion can be of a cylindrical configuration with a polygonal base surface. If that is the case, there is only one or a few specific connecting options with the holder which is preferably of a complementary configuration. Preferably, however, it is provided that the machining portion has a circular-cylindrical or partially conical outside contour so that there would actually not be a specific position for the machining portion relative to the holder. As however that is often important for calibration of the position of the machining portion, it is preferably provided that a positioning projection or a positioning groove is provided in the fixing region, wherein the positioning projection or the positioning groove in the condition of the machining portion of being mounted in the holder engages into a counterpart portion of a complementary configuration on the holder, preferably a fitment pin.

If the machining portion, in particular its machining region, is of a cylindrical shape, that cylinder can have a longitudinal axis which is not oriented perpendicularly to the circular or elliptical base surface, thereby providing an inclined cylinder. Preferably, however, the machining portion is at least partially in the form of a right circular cylinder. That provides that the surface of the machining region is at least partially in the shape of the peripheral surface of a circular cylinder, with a peripheral surface diameter, said peripheral surface diameter being twice as great as the maximum spacing of the surface of the machining region relative to the longitudinal axis.

It can particularly preferably be provided that the fixing region also has at least in part a preferably outwardly directed and thus convex surface in the form of the peripheral surface of a circular cylinder, with a peripheral surface diameter, wherein said diameter of the machining region is smaller at least in a region adjoining the fixing region, than the peripheral surface diameter of the fixing region in that region which adjoins the fixing projection and which faces away from the machining region. In other words, this means that the fixing region, more specifically the fixing projection, is the widest region of the machining portion.

In the preferred configuration, the machining portion is of a circular cross section both in the large part of the machining region and also in the large part of the fixing region. It can however also be provided that the fixing region and/or the machining region is/are at least partially of a rectangular, in particular square, cross section. In this respect also, in substance, the same considerations apply as in the case of a circular cross section, namely that the maximum diameter in the region of the fixing projection, as measured normal relative to the longitudinal axis, is greater than the maximum diameter of the machining region. In that way, expressed in simple terms, the fixing projection stands away from the machining region and the machining portion can be securely and precisely held by way of the fixing projection.

It is preferably provided that the fixing region and the machining region of the machining portion are in one piece. Thus, the machining portion—more specifically if it is a crown or a dental construction—forms only an individual block comprising a single material. In order to offer the possibility of the work being easier for the dental technicians, it is preferably provided that the machining portion, preferably at the end remote from the fixing region, has a prefabricated implant connection—which is separate from the machining region and the fixing region—for fixing the machining portion to a dental implant. In other words, the implant connection is arranged at the side of the machining portion, that is towards the fixing projection. The surface of the fixing projection thus so-to-speak "faces" in the direction of the implant connection. Depending on the respective dental implant type used, machining portions can also be correspondingly made available, with different kinds of implant connections.

To provide a stable structure of the abutment or machining portion, it is preferably provided that the spacing of the surface of the machining region, measured normal to the longitudinal axis and leading away from the longitudinal axis (and of the entire surface region adjoining the fixing projection) is at least 40%, preferably at least 70%, particularly preferably at least 90% and quite particularly preferably 100%, of the maximum spacing of the machinable surface. In other words, there is practically no narrow location in the entire region of the abutment, that adjoins the fixing projection in the direction of the machining region. Preferably, overall practically the entire surface region adjoining the fixing region involves a substantially constant spacing relative to the longitudinal axis. It is only in the end region (that is to say, towards the implant connection) that a rounded-off configuration can be provided or formed. That preferred embodiment applies in particular when the machining portion is of a circular cross section.

If the abutment is not of a circular cross section but is for example rectangular, then naturally at the corner regions the spacing relative to the longitudinal axis is substantially greater. In order here too to guarantee a stable structure, it is preferably provided that in any longitudinal section—that is to say in a section parallel to the longitudinal axis and through the longitudinal axis—the spacing of the surface of the machining region, measured normal to the longitudinal axis and leading away from the longitudinal axis (and of the surface of the fixing region adjoining the fixing projection in the direction of the machining region), is at least 40%, preferably at least 70%, particularly preferably 90%, and quite particularly preferably 100%, of the maximum spacing in the same longitudinal section of the machinable surface relative to the longitudinal axis. Thus, a high degree of stability is also achieved with abutments of polygonal section.

The machining portion is of a given machining portion length as measured along the longitudinal axis between the fixing region end and the machining region end. The fixing projection is arranged or provided at any desired location in itself between those two ends. To minimize the lever forces in machining the machining portion, the fixing projection should be as close to the machining region as possible. Preferably, the fixing projection is in the central half, particularly preferably in the central third of the machining portion. Accordingly, the spacing of the fixing projection relative to the fixing region end is between 20% and 50%, preferably between 35% and 45%, of the machining portion length while the spacing of the fixing projection relative to the machining region end is between 80% and 50%, preferably between 65% and 55% of the machining portion length. In that respect, it is also preferably provided that the spacing of the fixing projection relative to the machining region end is at a maximum 20%, preferably at a maximum 10%, of the machining portion length.

An axially elongate holder of a partially complementary configuration for holding a dental machining portion has a holding region for the dental machining portion, wherein provided in the holding region is a holding nose oriented transversely relative to the longitudinal axis, wherein, in the condition of the machining portion being mounted to the holder, the holding nose bears against a fixing projection which is of a complementary configuration on the machining portion, thereby giving a positively locking connection between the fixing projection and holding nose. A holder of that kind is known, for example, from US 2012/0214133 A1, wherein the screw head shown therein forms the holding nose. In order also to avoid the disadvantages of the state of the art for the holder, it is provided according to the invention that the holder has a base element and a cap nut which can be connected to the base element, preferably by way of a thread, wherein the holding region with holding nose is provided on the cap nut and the minimum spacing of the holding nose relative to the longitudinal axis, as measured normal to the longitudinal axis, is less than the minimum spacing, as measured normal to the longitudinal axis, of the remaining cap nut relative to the longitudinal axis. In that arrangement, the cap nut has an opening adapted to the machining region of the machining portion so that said machining region fits through the opening of the cap nut. The fixing region, in particular the fixing projection, is however of a diameter larger than the inside diameter of the opening in the cap nut so that the fixing projection bears against the cap nut, especially against the holding nose provided around the opening.

To clamp the machining portion to the holder as fixedly as possible, it is preferably provided that there is provided at least one flat location parallel to the longitudinal extent of the holder for the fitment of a tool and for fixing the machining portion to the cap nut. Naturally, it would alternatively be possible to provide only for manually tightening the cap nut.

For initial manual insertion of the machining portion on the holder, it is preferably provided that the base element has a conical region, wherein, in the condition of the machining portion being mounted to the holder, the conical region bears against a conical region of a complementary configuration on the machining portion.

Naturally, the holder itself also has to be fixed somewhere. For that purpose, there is preferably provided a fixing connection for fixing the holder to the machining device, more especially to a receiving device.

A set (having a machining portion according to the invention and a holder according to the invention) comprises a plurality of machining portions—possibly of different sizes, with different kinds of implant connections and with machining regions of differing sizes. That set is suitable, in particular, for permitting retrofitting to the new fixing method, in relation to dental machining devices which are already in existence or already in use.

A dental machining device has a housing, a receiving device connected to the housing, in particular moveably, for at least one holder of a dental machining portion, at least one holder according to the invention, at least one machining portion according to the invention which can be fixed in the holder and at least one machining head, in particular a milling cutter, grinding cutter or the like, for machining the machining portion. In that respect, it can preferably be provided that the at least one holder can be fixed to the receiving device by way of the fixing connection. That receiving device itself can be mounted moveably relative to the housing.

In order to know the position of the holder or the machining portion relative to the receiving device, there is preferably provided a calibration device, wherein the position of the at least one machining portion relative to the receiving device can be detected by the calibration device. That calibration device can also include a limit switch.

Further preferably, there can be provided a control or regulating unit, by which the machining head, a movement of the receiving device and/or the calibration device can be controlled or regulated. In that respect, in a preferred embodiment, the control or regulating unit forms a central interface for all controllable components which together form the dental machining device. Particularly preferably, that control or regulating unit also includes a memory in which various processing programs for performing various machining steps are stored.

The machining portion can comprise the following materials (or mixtures thereof): titanium, zirconium, aluminum, chrome-cobalt alloy, plastic and ceramic material.

BRIEF DESCRIPTION OF THE DRAWINGS

Further details and advantages of the present invention are described more fully hereinafter by means of the specific description with reference to the embodiments by way of example illustrated in the drawings in which:

FIGS. 1 through 5 show various views of a machining portion,

FIGS. 6 through 8 show various views of a receiving device with holders and machining portions, FIGS. 9 and 10 show a dental machining device with receiving devices, holders and machining portions, FIGS. 11 through 12b show various views of an alternative variant of a holder, FIGS. 13 through 16 show the dental machining device with the alternative holder, FIGS. 17 through 20 show various views of the holder with calibration device, FIGS. 21 and 22 show the holder with calibration device in a dental machining device, FIGS. 23 and 24 show a second embodiment of a machining portion, and FIGS. 25 through 30 show a machining portion in the form of a dental construction.

DETAILED DESCRIPTION OF THE INVENTION

Figure 2A:
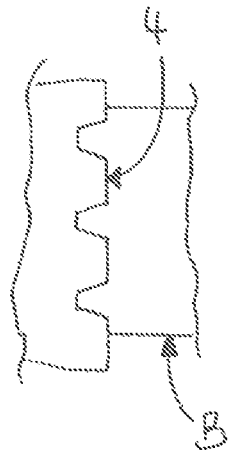

FIG. 1 shows a dental machining portion 1 in the form of an abutment. That abutment is preferably made from titanium. In principle, that machining portion 1 is subdivided into two regions, on the one hand into the fixing region F with the outwardly directed, substantially convexly shaped surface U and on the other hand into the machining region B with the outwardly directed, substantially convexly shaped surface S. In particular, the machining region B and its machinable surface S are machined by a dental machining device 2 which is also shown hereinafter. The fixing region F includes a conical region K1, an adjoining short circular-cylindrical region 21, thereafter the fixing projection 4 which is oriented at a 90 degrees angle relative to the circular-cylindrical region 21, and thereafter a short further circular-cylindrical region 22 of a smaller diameter than the circular-cylindrical region 21, that region 22 going directly into the machining region B. At the end remote from the fixing region F, the dental machining portion 1 has a prefabricated implant connection 8.

FIG. 2 once again shows those regions of the dental machining portion 1 as a side view. FIG. 2 additionally shows the longitudinal axis X, wherein the large part of the external contour of the dental machining portion 1 is of a rotationally symmetrical configuration around that longitudinal axis X. Only the implant connection 8 and the positioning groove 6 which is clearly visible in FIG. 3 are not rotationally symmetrical. That positioning groove 6 is also clearly visible in the section B-B shown in FIG. 4 and in the front view of FIG. 5.

Figure 2B:
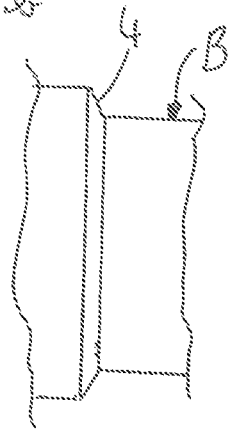
Figure 2C:
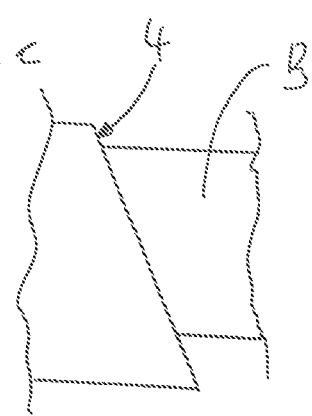

As shown in FIG. 1, the fixing projection 4 is a flat surface oriented at a right angle relative to the longitudinal axis X. Alternatively, however, the fixing projection can have recesses or uneven portions, with the holding nose 5 preferably being of a corresponding configuration. In that respect, attention is directed to FIG. 2b. The fixing projection 4 can also be inclined through about 30° relative to the longitudinal axis X, as shown in FIG. 2b. In addition, the overall orientation of the fixing projection can be inclined relative to the longitudinal axis X, as shown in FIG. 2c. At any event it is important that, by way of the fixing projection 4 oriented transversely relative to the longitudinal axis X, force can be applied from the holder 3 and its holding nose 5 to the machining portion 1, which acts to clamp it fast in the direction of the fixing region F.

FIG. 2 shows that the surface S of the machining region B, which in at least region-wise manner is in the form of the peripheral surface of a circular cylinder, and has a spacing T measured normal relative to the longitudinal axis X. The maximum spacing $T_{max}$ is the same in the entire portion of the machining region B, that is in the shape of a circular cylinder. The fixing projection 4 or portions of the surface U of the fixing region F also has or have a spacing R relative to the longitudinal axis X, as measured normal relative to the longitudinal axis X. That spacing $R_{max}$ is at a maximum in the fixing projection 4 or in the circular-cylindrical region 21. According to the invention, a maximum spacing $T_{max}$ of the surface S is less than the maximum spacing $R_{max}$ of the surface U or of the fixing projection 4 relative to the longitudinal axis X. That affords an outwardly directed stable abutment for a holder 3 directly on the machining portion 1 itself.

As is clearly visible in FIGS. 2 and 3, the short circular-cylindrical region 22 forms that region that adjoins the fixing projection 4 and faces towards the machining region B, whereas the circular-cylindrical region 21 is provided in the region G which faces away from the machining region B and adjoins the fixing projection 4.

In that region G, the fixing region F is of the maximum peripheral surface diameter $D_F$ (see FIG. 3). The region E is disposed in the machining region B, adjoining the fixing region F. In that region E, the machining region B involves its maximum peripheral surface diameter $D_B$ which is less than the maximum diameter $D_F$ in the region G of the fixing region F.

FIG. 6 shows how dental machining portions 1 are fixed to holders 3. For the fixing operation, the dental machining portion 1 is firstly inserted into the holder 3, with the fixing region F leading. In that respect, the base element 9 of the holder 3 has a conical region $K_3$ which is of a complementary configuration to the conical region $K_1$ of the machining portion 1. In that case, the machining portion 1 can only be entirely introduced as far as the condition of abutment against the conical region $K_3$ in a specific position, namely only when the positioning groove 6 in the machining portion 1 is so introduced that it can receive the fitting pin 7 arranged on the holder 3. Naturally, in the converse fashion, a fitting projection on the machining portion 1 can also engage into a groove provided on the holder 3. If the dental machining portion 1 has been inserted into the holder 3, in that way that already affords precise centering. However, there is still not a sufficient clamping force for machining the machining portion 1. For that purpose, the cap nut 11 which together forms the holder 3 is used. The nut 11 has an opening 23 through which, in particular, the machining region B of the machining portion 1 fits. In the region of the holding nose 5, the cap nut 11 has the minimum spacing $P_{min}$, as measured normal to the longitudinal axis X, whereas the minimum spacing $Q_{min}$ as measured normal to the longitudinal axis X of the rest of the cap nut 11 with respect to the longitudinal axis X is greater. As soon as the cap nut 11 bears against the base element 9, those two components can be connected together by way of the thread 10. In that case, the tightening turning operation is performed until the holding nose 5 on the cap nut 11 bears firmly against the fixing projection 4 of the machining portion 1 and thereby clamps the dental machining portion 1 firmly to the holder 3. In that way, the dental machining portion 1 is clamped fixedly by way of its fixing region F to the complementary holding region H of the holder 3. As shown in FIG. 6, there are three such holders 3 and three such machining portions 1 which are respectively mounted to the receiving device 16 by way of a fixing connection 14.

Further views of that receiving device 16 with holders 3 and machining portions 1 are shown in FIGS. 7 and 8. FIGS. 7 and 8 also show a plurality of openings 24 in the receiving device 16, which serve, in particular, for determining the position of the overall receiving device 16 relative to the machining device 2. The receiving device 16 is oriented by way of a positioning means in the machining device 2 and is then fixed by way of a fixing or clamping mechanism. The receiving device 16 can be mounted moveably to the machining device 2. The connection between the holder 3 and the receiving device 16 can be implemented by way of a thread, by way of a fitting pin, by way of an adhesive join, by way of pressing or, for example, by shrink fitment.

That can also be seen from FIGS. 9 and 10 showing the machining device 2 with the housing 15. In this case, a plurality of machining heads 17 are also disposed in the housing 15. The receiving device 16 is preferably moveable in at least three degrees of freedom relative to the housing 15 by way of a plurality of drives and joints or spindles.

FIG. 11 shows an alternative embodiment of a holder 3, wherein, in particular, the base element 9 is of an alternative configuration in the region remote from the machining portion 1. In principle, the base element 9 itself again has a male thread as part of the cap nut 11 and the conical region $K_3$. It is also possible to see the fitting pin 7. The cap nut 11 and the machining portion 1 are practically identical to the first embodiment. As a substantial difference, the limit switch 20 can also be fixed to the base element 9, as can be seen, in particular, from FIG. 12. That limit switch 20 corresponds to an abutment disposed on the machine. Conversely, the abutment instead of the limit switch 20 can also be arranged on the base element 9. The section A-A shown in FIG. 12a is also clearly illustrated in FIG. 12b, wherein, besides the fixing projection 9 and the holding nose 5, it is also possible to see in this sectional view the fitting pin 7 which engages into the positioning groove 6. The limit switch 20 is also shown as a section.

FIGS. 13 and 14 show this embodiment of a holder 3 when mounting the machining portion 1 by means of the cap nut 11 and the tool 13. More especially, that tool 13 engages the flat locations 12 of the cap nut. In that way, the machining portion 1 can be clamped fast to the holder 3.

The tool 13 has been removed again in FIGS. 15 and 16. The limit switch 20 can correspond to a counterpart portion mounted in the region of the housing 15 and can thereby define the precise position (as already mentioned, the reversed arrangement is also possible). In this case, a drill is provided as the machining head 17. That drill can also be changed by way of the tool magazine 25.

Instead of the dental machining portion 1, FIG. 17 shows the calibration device 18 having a block 27 with a conical region $K_1$ and the fixing screw 26. When those parts are assembled as shown in FIGS. 18, 19 and 20, it is possible to determine the precise position relative to the machining device 2. For that purpose, the machining device 2 with a sensing member (not shown) senses the geometrical shape of the block 27. As a further consequence, that position is then communicated by the calibration device 18 to the control or regulating unit 19 diagrammatically shown in FIGS. 21 and 22. When then that calibration device 18 is removed again, it is possible to use any desired machining portion 1 and the position of the holder 3 or the machining portion 1 relative to the housing 15 is precisely known. The values detected by way of the calibration device 18 are stored in the software of the control or regulating unit 19 in order to be able to perform the later calculations on the basis thereof. In order not to have to always perform that calibration step, there is the limit switch 20 which is actuated upon rotation of the entire receiving device 16. That position relative to the calibration device 18 is also stored in the control or regulating unit 19. When then a fresh blank or a fresh abutment is used, the receiving device 16 is rotated in a given direction until the limit switch 20 produces a signal. At that moment, the control or regulating unit 19, by virtue of the storage values, then again recognizes the position in which the abutment or the machining portion 1 is disposed in the overall machining device 2.

FIGS. 23 and 24 show a second embodiment of a machining portion 1. With this or also another kind of external geometry, it is possible to carry out a scan prior to the machining operation (that is to say, prior to the cutting process) with that machining portion 1. Hitherto, separate scan markers have been used to determine the position and inclination of the implants disposed in the jaw of the patient. A machining portion 1 involving the external geometry as shown in FIGS. 23 and 24 can be used in non-machined form, as such a scan marker. Then, in a second step, the desired part is milled in the machining device 2.

FIG. 25 shows a dental machining portion 1 in the form of a dental construction which is as yet unmachined. In that respect, in substance, the same advantages and variants apply in terms of fixing and manufacture, as for the abutment. In particular, the fixing region F is of the same dimensions. The machining region B can possibly be of a larger diameter than in the case of the abutment, in which respect the provision must still apply that the maximum spacing $T_{max}$ of the surface S of the machining region B relative to the longitudinal axis X is less than the maximum spacing $R_{max}$ of the fixing projection 4 relative to the longitudinal axis X. The views in FIGS. 26 and 27 correspond in substance to FIGS. 2 and 3, in which respect the dental machining portion 1 in the fixing region F can also be of a non-hollow configuration, in contrast to FIG. 4.

In FIGS. 28 through 30, the machining region B of the dental machining portion 1 has been machined, whereby it is now possible to see a dental construction.

The invention claimed is:

1. An axially elongate dental machining portion, comprising:
   a machining region machinable by a dental machining device, and
   a fixing region for fixing the axially elongate dental machining portion to a holder of the dental machining device,
   wherein a fixing projection projects from the fixing region such that the fixing projection is oriented transversely relative to a longitudinal axis of the axially elongate dental machining portion such that, when the axially elongate dental machining portion is mounted in the holder, the fixing projection bears against a holding nose positioned in complementary relationship on the holder, the machining region having a machinable surface which has a maximum spacing relative to the longitudinal axis of the axially elongate dental machining portion, measured normal to the longitudinal axis of the axially elongate dental machining portion, and the fixing projection having a maximum spacing relative to the longitudinal axis of the axially elongate dental machining portion, measured normal relative to the longitudinal axis of the axially elongate dental machining portion, that is greater than the maximum spacing of the machinable surface relative to the longitudinal axis of the axially elongate dental machining portion, and
   wherein the fixing region includes:
     a conical region having a conical surface,
     a first cylindrical region having a cylindrical surface directly adjoining the conical surface, the fixing projection directly adjoining the first cylindrical region, and being oriented at an angle of 90 degrees relative to the first cylindrical region, and
     a second cylindrical region of a smaller diameter than the first cylindrical region, the second cylindrical region directly adjoining the fixing projection and extending directly to the machining region.

2. The axially elongate dental machining portion as set forth in claim 1, wherein the fixing projection is oriented at an angle of 90 degrees relative to the longitudinal axis of the axially elongate dental machining portion.

3. The axially elongate dental machining portion as set forth in claim 1, wherein the fixing projection is of an annular configuration on the axially elongate dental machining portion.

4. The axially elongate dental machining portion as set forth in claim 1, wherein the machinable surface of the machining region is at least partially a peripheral surface of a circular cylinder of the machining region, and wherein a diameter of the circular cylinder of the machining region is twice as great as the maximum spacing of the machinable surface of the machining region relative to the longitudinal axis of the axially elongate dental machining portion.

5. The axially elongate dental machining portion as set forth in claim 4, wherein the diameter of the circular cylinder of the machining region, at least in a part of the machining region adjoining the fixing region, is less than a diameter of the first cylindrical region of the fixing region.

6. The axially elongate dental machining portion as set forth in claim 1, wherein the conical region, when the axially elongate dental machining portion is mounted in the holder, bears against a conical region of a complementary configuration on the holder.

7. The axially elongate dental machining portion as set forth in claim 1, wherein a positioning groove is defined in the fixing region, and wherein the positioning groove, when the axially elongate dental machining portion is mounted in the holder, bears against a counterpart portion of a complementary configuration on the holder.

8. The axially elongate dental machining portion as set forth in claim 7, wherein the counterpart portion is a fitting pin.

9. The axially elongate dental machining portion as set forth in claim 1, wherein the axially elongate dental machining portion has an implant connection for fixing the axially elongate dental machining portion to a dental implant.

10. The axially elongate dental machining portion as set forth in claim 9, wherein the implant connection is at an end of the axially elongate dental machining portion remote from the fixing region.

11. The axially elongate dental machining portion as set forth in claim 1, wherein each of a spacing of the machinable surface of the machining region from the longitudinal axis of the axially elongate dental machining portion and measured normal to the longitudinal axis of the axially elongate dental machining portion, and a spacing of a surface of the fixing region from the longitudinal axis of the axially elongate dental machining portion and measured normal to the longitudinal axis of the axially elongate dental machining portion, that adjoins the fixing projection in a direction of the machining region, is at least 40% of the maximum spacing of the machinable surface relative to the longitudinal axis of the axially elongate dental machining portion.

12. The axially elongate dental machining portion as set forth in claim 11, wherein each of the spacing of the machinable surface of the machining region from the longitudinal axis of the axially elongate dental machining portion and measured normal to the longitudinal axis of the axially elongate dental machining portion, and the spacing of the surface of the fixing region from the longitudinal axis of the axially elongate dental machining portion and measured normal to the longitudinal axis of the axially elongate dental machining portion, that adjoins the fixing projection in the direction of the machining region, is at least 70% of the maximum spacing of the machinable surface relative to the longitudinal axis of the axially elongate dental machining portion.

13. The axially elongate dental machining portion as set forth in claim 12, wherein each of the spacing of the machinable surface of the machining region from the longitudinal axis of the axially elongate dental machining portion and measured normal to the longitudinal axis of the axially elongate dental machining portion, and the spacing of the surface of the fixing region from the longitudinal axis of the axially elongate dental machining portion and measured normal to the longitudinal axis of the axially elongate dental machining portion, that adjoins the fixing projection in the direction of the machining region, is at least 90% of the maximum spacing of the machinable surface relative to the longitudinal axis of the axially elongate dental machining portion.

14. The axially elongate dental machining portion as set forth in claim 1, wherein the axially elongate dental machining portion has a cross section differing from a circular shape in a longitudinal section, each of a spacing of the machinable surface of the machining regional from the longitudinal axis of the axially elongate dental machining portion and measured normal to the longitudinal axis of the axially elongate dental machining portion, and a spacing of a surface of the fixing region from the longitudinal axis of the axially elongate dental machining portion and measured normal to the longitudinal axis of the axially elongate dental machining portion, that adjoins the fixing projection in a direction of the machining region, is at least 40% of the maximum spacing in the longitudinal section of the machinable surface relative to the longitudinal axis of the axially elongate dental machining portion.

15. The axially elongate dental machining portion as set forth in claim 14, wherein each of the spacing of the machinable surface of the machining region from the longitudinal axis of the axially elongate dental machining portion and measured normal to the longitudinal axis of the axially elongate dental machining portion, and the spacing of the surface of the fixing region from the longitudinal axis of the axially elongate dental machining portion and measured normal to the longitudinal axis of the axially elongate dental machining portion, that adjoins the fixing projection in the direction of the machining region, is at least 70% of the maximum spacing in the longitudinal section of the machinable surface relative to the longitudinal axis of the axially elongate dental machining portion.

16. The axially elongate dental machining portion as set forth in claim 15, wherein each of the spacing of the machinable surface of the machining region from the longitudinal axis of the axially elongate dental machining portion and measured normal to the longitudinal axis of the axially elongate dental machining portion, and the spacing of the surface of the fixing region from the longitudinal axis of the axially elongate dental machining portion and measured normal to the longitudinal axis of the axially elongate dental machining portion, that adjoins the fixing projection in the direction of the machining region, is at least 90% of the maximum spacing in the longitudinal section of the machinable surface relative to the longitudinal axis of the axially elongate dental machining portion.

17. The axially elongate dental machining portion as set forth in claim 1, wherein the axially elongate dental machining portion has a machining portion length as measured along the longitudinal axis of the axially elongate dental machining portion between a fixing region end and a machining region end, and the fixing projection is positioned between those two ends, wherein a spacing of the fixing projection relative to the fixing region end is between 35% and 45% of the machining portion length or a spacing of the fixing projection relative to the machining region end is between 65% and 55% of the machining portion length.

18. A set comprising:
the axially elongate dental machining portion as set forth in claim 1; and
a holder including a holding region for holding the axially elongate dental machining portion, wherein included in the holding region is a holding nose oriented transversely relative to the longitudinal axis of the axially elongate dental machining portion, wherein, when the axially elongate dental machining portion is mounted to the holder, the holding nose bears against a fixing projection of complementary configuration on the axially elongate dental machining portion, wherein the holder has a base element and a cap nut which can be connected to the base element, wherein the holding nose is on the cap nut and a minimum spacing of the holding nose relative to the longitudinal axis of the axially elongate dental machining portion, measured normal relative to the longitudinal axis of the axially elongate dental machining portion, is less than a minimum spacing of a remainder of the cap nut relative to the longitudinal axis of the axially elongate dental machining portion, measured normal relative to the longitudinal axis of the axially elongate dental machining portion.

19. A dental machining device comprising:
the set as set forth in claim 18;
a housing;
a receiving device connected to the housing for receiving the holder of the set; and
a machining head for machining the axially elongate dental machining portion.

20. The machining device as set forth in claim 19, wherein the holder can be fixed to the receiving device by a fixing connection.

21. The machining device as set forth in claim 19, further comprising a calibration device configured to determine a position of the axially elongate dental machining portion relative to the receiving device.

22. The machining device as set forth in claim 21, further comprising a control or regulating unit for controlling or regulating at least one of the machining head, the receiving device, and the calibration device.

23. The dental machining device as set forth in claim 19, wherein the receiving device is moveably connected to the housing.

24. The dental machining device as set forth in claim 19, wherein the machining head is a milling cutter or a grinding cutter.

25. An axially elongate dental machining portion, comprising:
a machining region machinable by a dental machining device, and
a fixing region for fixing the axially elongate dental machining portion to a holder of the dental machining device,
wherein a fixing projection surface projects from the fixing region such that the fixing projection surface is oriented transversely relative to a longitudinal axis of the axially elongate dental machining portion such that, when the axially elongate dental machining portion is mounted in the holder, the fixing projection surface bears against a holding nose positioned in complementary relationship on the holder, the machining region having a machinable surface which has a maximum spacing relative to the longitudinal axis of the axially elongate dental machining portion, measured normal to the longitudinal axis of the axially elongate dental machining portion, and the fixing projection surface having a maximum spacing relative to the longitudinal axis of the axially elongate dental machining portion, measured normal relative to the longitudinal axis of the axially elongate dental machining portion, that is greater than the maximum spacing of the machinable surface relative to the longitudinal axis of the axially elongate dental machining portion, and wherein the fixing region includes:
- a front side which is oriented transversely relative to the longitudinal axis of the axially elongate dental machining portion,
- a conical region having a conical surface and directly adjoining the front side,
- a first cylindrical region having a cylindrical surface directly adjoining the conical surface, the fixing projection surface directly adjoining the first cylindrical region, and being oriented at an angle of between 45 and 135 degrees relative to the first cylindrical region, and
- a second cylindrical region of a smaller diameter than the first cylindrical region, the second cylindrical region directly adjoining the fixing projection surface and extending directly to the machining region, and wherein the conical region, between the front side and the first cylindrical region, has a constant angle relative to the longitudinal axis of the axially elongate dental machining portion from a first area of the conical region directly adjoining the front side to a second area of the conical region directly adjoining the first cylindrical region.

* * * * *